United States Patent [19]
Knebel et al.

[11] Patent Number: 6,008,371
[45] Date of Patent: Dec. 28, 1999

[54] PROCESS FOR THE PREPARATION OF (METH)ACRYLIC ACID ESTERS

[75] Inventors: Joachim Knebel, Darmstadt; Ralf Merbach, Buettelborn, both of Germany

[73] Assignee: Roehm GmbH, Darmstadt, Germany

[21] Appl. No.: 09/091,236

[22] PCT Filed: Nov. 13, 1996

[86] PCT No.: PCT/DE96/02161

§ 371 Date: Jun. 16, 1998

§ 102(e) Date: Jun. 16, 1998

[87] PCT Pub. No.: WO97/22592

PCT Pub. Date: Jun. 26, 1997

[30] Foreign Application Priority Data

Dec. 16, 1995 [DE] Germany .................. 195 47 099

[51] Int. Cl.[6] ............................................. C07D 233/32
[52] U.S. Cl. ............................................. 548/324.1
[58] Field of Search ................................ 548/324.1

[56] References Cited

U.S. PATENT DOCUMENTS

| | | | |
|---|---|---|---|
| 3,194,792 | 7/1965 | Emmons et al. | 548/324.1 X |
| 3,356,653 | 12/1967 | Sekmakas | 548/324.1 X |
| 4,777,265 | 10/1988 | Merger et al. | 548/324.1 |
| 4,845,233 | 7/1989 | Higuchi et al. | 548/324.1 |
| 5,210,199 | 5/1993 | Grosius et al. | 548/324.1 |
| 5,498,723 | 3/1996 | Riondel et al. | 548/324.1 |
| 5,567,826 | 10/1996 | Knebbl et al. | 548/324.1 |
| 5,610,313 | 3/1997 | Riondel et al. | 548/324.1 |
| 5,744,613 | 4/1998 | Riondel et al. | 548/324.1 |

FOREIGN PATENT DOCUMENTS

| | | |
|---|---|---|
| 0236994 | 9/1987 | European Pat. Off. . |
| 0571851 | 12/1993 | European Pat. Off. . |
| 0619309 | 10/1994 | European Pat. Off. . |
| 0650962 | 5/1995 | European Pat. Off. . |

OTHER PUBLICATIONS

Hamamoto et al, Chemical Abstracts, vol. 84, # 136271f, 1976.

*Primary Examiner*—Floyd D. Higel
*Attorney, Agent, or Firm*—Oblon, Spivak, McClelland, Maier & Neustadt, P.C.

[57] ABSTRACT

A catalytic process for the preparation of (meth)acrylic acid esters of formula (I), in which R1 is H or $CH_3$ and A and B are unbranched or branched alkylene groups with 2 to 5 C-atoms, by reaction of (meth)acrylic acid esters of formula (II), in which $R_2$ is an alkyl group of in particular 1 to 4 C-atoms, and alcohols of formula (III) in the presence of a maximum of 250 ppm $Ca(OH)_2$ as the catalyst. After reaction the catalyst can be separated from the reaction mixture by filtration.

4 Claims, No Drawings

PROCESS FOR THE PREPARATION OF (METH)ACRYLIC ACID ESTERS

This application is a PCT/DE96/02161 filed Nov. 13, 1996.

FIELD OF THE INVENTION

The present invention relates to a new and improved process for the production of acrylic or methacrylic acid esters with the formula

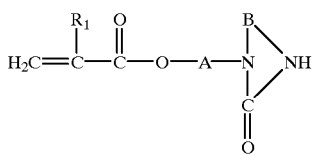

in which $R_1$ stands for hydrogen or a methyl group and A and B stand for unbranched or branched alkylene groups with 2 to 5 C atoms.

State of the Art

Compounds of Formula I can be obtained in accordance with the process described in the U.S. Pat. No. 2,871,223, by means of reaction of acrylic or methacrylic acid chloride with hydroxyalkyl imidazolidine-2-ones in the presence of tertiary nitrogen bases, with stoichiometric amounts of the hydrochlorides of the tertiary nitrogen bases being formed, along with other products.

In the process known from EP 0 236 994 A1, for the production of acryl and methacryl esters of Formula I, acrylic or methacrylic acid esters are reacted with 1-(hydroxyalkyl) imidazolidine-2-ones in the presence of titanium alcoholates or chelate compounds of the metals titanium, zirconium, iron, and zinc, with 1,3-dicarbonyl compounds as the re-esterification catalysts.

In EP-A 0 433 135 and EP-A 0 453 638, diorgano tin oxide compounds are claimed as re-esterification catalysts for the re-esterification of acryl and methacryl esters with hydroxyalkyl imidazoline-2-ones.

As a rule, the metal catalyst must be removed from batches after the reaction is complete. This is advantageously done by adding water, for example when using tetraalkyl titanates or dialkyl tin oxides. In this connection, the titanates form metal (hydr)oxides, such as $TiO_2$, which are removed by filtering or centrifuging them off, for example. These hydrolyzed re-esterification catalysts cannot be used again as such after being removed. It is true that the dialkyl tin oxides can be removed as such by the addition of water, and can be used again as re-esterification catalysts. However, a relatively large amount of water has to be introduced, at first, and this has to be removed from the reaction product once again. According to the German patent application P 42 17 124.5, the reaction can also be carried out in the presence of mixtures of alkali/earth alkali metal compounds, which are essentially used as oxides, hydroxides, carbonates, and/or as salts of carboxylic acids. The alkali/earth alkali compounds present as catalysts can be removed without adding water. The amount of catalytically active compound mixtures is 0.01–10 wt.-%, with reference to the reaction mixture. In spite of the advantageously high reaction speed which is achieved with alkali/earth alkali catalysts, these systems stagnate after approximately 80% hydroxyalkyl imidazolidine-2-one conversion, so that the residual alcohol content in the reaction mixture is relatively high.

Also, the formation of N-(methacryloyl oxyethyl)-N'-(methacryloyl) ethylene urea, a bifunctional methacryl compound, which therefore has a cross-linking effect during polymerization reactions, is very high, at approximately 10% of the re-esterification compounds, and must be improved to be at lower proportions.

DE-OS 3013927 (BASF) describes a polymer-analog reaction with approximately 100,000 ppm calcium hydroxide as the catalyst.

DE 2238208 describes the re-esterification of bactericide quinoxaline derivatives with calcium hydroxide or barium hydroxide catalysis.

Task and Solution

The invention was based on the task of finding a catalytic process for the production of acrylic or methacrylic acid esters of Formula I by alcoholysis of (meth)acrylic acid alkyl esters with hydroxyalkyl imidazolidine-2-ones, which proceeds at a good reaction speed even in the region of final re-esterification, and in which the catalyst used can be removed from the reaction mixture without adding water and used again as such, if necessary. It was now found that the reaction can be carried out in surprisingly advantageous manner with calcium hydroxide, in an amount of less than 250 ppm, with reference to the total amount of the reaction mixture.

The invention relates to a process for the production of (meth)acryl esters of the formula I

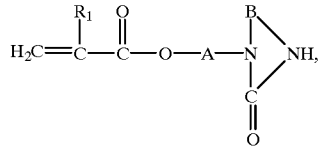

in which $R_1$ stands for hydrogen or a methyl group and A and B stand for unbranched or branched alkylene groups with 2 to 5 C atoms, by reaction of an acrylic acid ester or methacrylic acid ester of Formula II

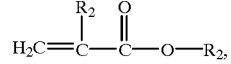

in which $R_1$ is as defined above and $R_2$ stands for an alkyl radical with 1 to 4 C atoms, with a heterocyclic compound of the Formula III

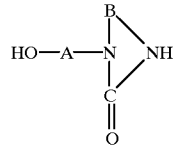

wherein A and B are as defined above, which is characterized by the fact that the reaction of an ester in accordance with Formula II with a heterocyclic compound of Formula III is carried out to produce an acryl or methacryl ester of Formula I in the presence of a catalyst which consists of calcium hydroxide.

A particular advantage of the new process is that high rates of conversion are achieved, and that the catalyst system which contains calcium, which is slurried up quantitatively, to a great extent, in the reaction mixture, can be removed without adding water (we added Tonsil), for example by filtration. Tonsil is used as an aid for removing dissolved catalyst (supplier: Südchemie AG).

Compounds of Formula I are valuable comonomers and are used, for example, in the production of polymer dispersions from vinyl monomers, which are primarily used as binders in paints, for example, or as leather processing aids. Comonomers of Formula I impart a desired hydrophilia to copolymerizates, and can function as formaldehyde scavengers in heat-curable resins with their imide group.

The success of the process according to the invention is surprising, since NH grouping of a compound of Formula II was to be expected in the presence of the catalyst, because of the bifunctionalities of I and III, during their reaction in further reactions, such as addition reactions analogous to a Michael addition to the double bond, or in amide formation by reaction of the acryl or methacryl ester of Formula I. The reaction of acryl and methacryl esters of Formula II with the alcohols of Formula III, according to the invention, proceeds very selectively to produce compounds of Formula I. According to the process according to the invention, process products of Formula I are obtained, which can be used without costly and qualitatively burdensome removal processes, directly, for example as a solution in the acryl or methacryl ester II, for use as comonomers, particularly in the production of dispersion polymerizates. Compounds I can also be produced as solids according to the present process, for example by being evaporated from solution.

Implementation of the Invention

For production of the compounds I in accordance with the process according to the invention, acrylic or methacrylic acid esters of Formula II are used, in which $R_2$ particularly stands for an alkyl radical with I to 4 carbon atoms. As examples, propyl acrylate, n-butyl acrylate, ethyl methacrylate, i-propyl methacrylate, i-butyl methacrylate, n-butyl methacrylate, and particularly methyl methacrylate should be mentioned.

As starting substances of Formula III, such compounds in which A or B represent a branched or unbranched alkylene group with 2 to 5 carbon atoms, e.g. $—(CH_2)_2—$, $—(CH_2)_3—$, $—(CH_2)_4—$, $—CH_2CH(CH_3)CH_2—$, $—CH_2C(CH_3)_2CH_2—$, are possible.

The number of ring elements of the heterocycle is preferably 5 and 6. It is particularly advantageous to use 1-(2-hydroxyethyl)-imidazolidine-2-one, which can be easily produced on a technical scale, for example, in accordance with U.S. Pat. No. 3,254,075, from aminoethyl ethanolamine and urea, as compound III.

As calcium compounds which are added to the reaction system as catalysts or catalyst-forming precursors, the bivalent calcium compounds, such as calcium hydroxide, should be mentioned. It is practical to use the calcium compounds which form the catalyst, i.e. the catalyst system, in catalytic amounts, in general not more than 250 ppm with reference to the sum of the reaction partners II and III. A high selectivity of product I with $R_1=CH_3$, A and $B=—(CH_2)_2—$ is achieved, for example, with 250 ppm $Ca(OH)_2$ with reference to the total amount of reaction mixture, in the re-esterification of methyl methacrylate with the corresponding compound III.

It is advantageous if the catalysts are used in fine dispersion, for example in powder or microcrystalline form. The reaction of acryl esters and/or methacryl esters of Formula II with the alcohols of Formula III (alcoholysis) is carried out at temperatures between 30 and 180 degrees C., particularly between 50 and 130 degrees C., in the presence of not more than 250 ppm of the calcium compound, calculated on the basis of the weight of the reaction mixture.

According to the equation, equimolar amounts of the reaction partners II and III react to form the desired end products I. In practice, however, it has proven to be practical to always keep the starting esters II in excess during the reaction. They are used in amounts of 1 to 20, preferably 2 to 10, particularly 3 to 6 moles per mole III.

To avoid polymerization losses, it is practical to carry out the reaction and processing of the reaction mixture in the presence of polymerization inhibitors such as phenothiazine, hydroquinone monomethyl ether, and particularly oxygen.

The reaction can take place under standard pressure, greater pressure, or in a partial vacuum. It can take place discontinuously or continuously. The starting substances II and III, for example, are heated to boiling together, in the presence of calcium compounds, and in this connection, the alcohol $R_2OH$ which is split off is continuously distilled off with the ester II, possibly in the form of its azeotrope. Depending on the reaction temperature, the catalyst, and the catalyst amount, the reaction times range from approximately 2 to 10 hours. It is also possible to carry out the reaction in the presence of an inert solvent, for example toluene or cyclohexane, but this is normally not necessary.

After completion of the reaction, excess monomer ester II can be removed completely or partially, by distilling it off. The dispersed catalyst is usually removed by filtration, and it is advantageous to do so before distilling off the monomer ester II, which is mostly present in excess. However, it can also be removed only after partial or complete removal of excess monomer ester II. The catalyst, which is recovered in the filtered form, can then be used in other alcoholysis batches, if necessary after being dried.

A preferred reaction product is one that is formed from methyl methacrylate and 1-(2-hydroxyethyl)-imidazolidine-2-one (hydroxyethyl ethylene urea) and therefore corresponds to Formula I with $R_1=CH_3$, $A=—(CH_2)_2—$ and $B=—(CH_2)_2—$.

EXAMPLES

Example 1

1100 g (11 mol) methyl methacrylate, 286 g (2.2 mol) hydroxyethyl ethylene urea, and 0.35 g hydroquinone monomethyl ether as well as 0.09 g phenothiazine as inhibitors are placed in a 2 liter round flask with mechanical stirring, air introduction, sump temperature display, and a filling element column (diameter: 35 mm, height 55 cm, 8×8 mm—Raschig rings) set on it, as well as an automatic column head with reflux and distillate cooler. The mixture is heated to boiling and first a methyl methacrylate water azeotrope is distilled off via the column, until the head temperature reaches 99° C. The batch is cooled by about 10° C., 0.35 g calcium hydroxide and the mass of methyl methacrylate which is equivalent to the azeotrope distillate are added. Again, the mixture is heated to boiling, and the resulting methyl methacrylate methanol azeotrope is distilled off at a reflux ratio of 2:1, up to a maximum head temperature of 70° C., later at a reflux ratio of 10:1, until a constant head temperature (99° C.) is reached. The reaction is terminated after 6 h. The batch is cooled to 80° C. and adjusted to a 25% solution of the product in methyl methacrylate by adding methyl methacrylate up to a total mass of 1742 g. 3.5 g Tonsil L80FF (Südchemie) are added, and the batch is clarified by pressure filtration (Seitz pressure filter, diameter —14 cm, filter layer T 1000 (Seitz) p<0.4 bar). The filtrate has the following composition, according to gas chromatography analysis:

| | |
|---|---|
| methyl methacrylate: | 72.5% |
| hydroxyethyl ethylene urea: | 1.4% |
| methacryloyl oxyethyl ethylene urea: | 23.7% |
| N-(methacryloyl oxyethyl)-N'-(methacryloyl) ethylene urea: | 1.2% |

Example 2

Carried out as Example 1, but leaving out the water removal step. Reaction time: 5.3 h.
The product is composed as follows, according to gas chromatography analysis:

| | |
|---|---|
| methyl methacrylate: | 71.8% |
| hydroxyethyl ethylene urea: | 1.7% |
| methacryloyl oxyethyl ethylene urea: | 24.0% |
| N-(methacryloyl oxyethyl)-N'-(methacryloyl) ethylene urea: | 1.2% |
| Platinum cobalt color number: | 22 |
| Acid number: | 0.05 |

Example 3

Carried out as Example 2, but using 0.55 g calcium hydroxide. Reaction time: 5.5 h.
The product has the following composition, according to gas chromatography analysis:

| | |
|---|---|
| methyl methacrylate: | 70.5% |
| hydroxyethyl ethylene urea: | 1.0% |
| methacryloyl oxyethyl ethylene urea: | 24.4% |
| N-(methacryloyl oxyethyl)-N'-(methacryloyl) ethylene urea: | 2.0% |

Example 4

Carried out as in Example 2, but using 0.28 g (200 ppm relative to the total amount weighed in) calcium hydroxide. Reaction time: 6.0 h.
The product has the following composition, according to gas chromatography analysis:

| | |
|---|---|
| methyl methacrylate: | 71.3% |
| hydroxyethyl ethylene urea: | 1.6% |
| methacryloyl oxyethyl ethylene urea: | 25.1% |
| N-(methacryloyl oxyethyl)-N'-(methacryloyl) ethylene urea: | 0.7% |

It is claimed:

1. Process for the production of (meth)acryl esters of the Formula I

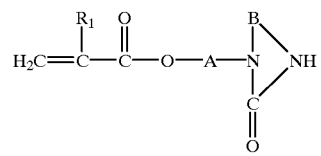

in which $R_1$ stands for hydrogen or a methyl group and A and B stand for unbranched or branched alkylene groups with 2 to 5 C atoms comprising: reacting an acrylic acid ester or methacrylic acid ester of Formula II

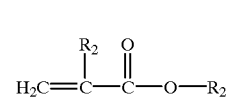

in which $R_1$ is as defined above and $R_2$ stands for an alkyl radical with 1 to 4 C atoms, with a heterocyclic compound of the Formula III

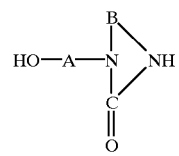

wherein A and B are as defined above, to produce an acryl or methacryl ester of Formula I in the presence of 1–250 ppm, based on the total reaction mixture, of a catalyst which contains calcium hydroxide.

2. The process of claim 1, wherein the amount of catalyst is 10 ppm to 150 ppm.

3. The process of claim 1, wherein the compound of Formula III is 1-(2-hydroxyethyl)-imidazolidine-2-one.

4. The process of claim 1, wherein the compound of Formula II is methylmethacrylate.

* * * * *